United States Patent
Rahn et al.

(10) Patent No.: US 7,613,499 B2
(45) Date of Patent: Nov. 3, 2009

(54) METHOD AND SYSTEM FOR CONCURRENT LOCALIZATION AND DISPLAY OF A SURGICAL CATHETER AND LOCAL ELECTROPHYSIOLOGICAL POTENTIAL CURVES

(75) Inventors: Norbert Rahn, Forchheim (DE); Arne Westphal, Adelsdorf (DE)

(73) Assignee: Siemens Aktiengesellschaft, Munich (DE)

( * ) Notice: Subject to any disclaimer, the term of this patent is extended or adjusted under 35 U.S.C. 154(b) by 74 days.

(21) Appl. No.: 11/392,035

(22) Filed: Mar. 29, 2006

(65) Prior Publication Data

US 2006/0241421 A1  Oct. 26, 2006

(30) Foreign Application Priority Data

Mar. 30, 2005  (DE) .................. 10 2005 014 854

(51) Int. Cl.
*A61B 5/04* (2006.01)

(52) U.S. Cl. .................. 600/426; 600/424; 600/427; 600/509

(58) Field of Classification Search ............. 604/95; 600/420, 424, 426, 427, 373, 481, 509
See application file for complete search history.

(56) References Cited

U.S. PATENT DOCUMENTS

| | | | | |
|---|---|---|---|---|
| 5,443,489 A | * | 8/1995 | Ben-Haim | ............ 607/115 |
| 5,738,096 A | * | 4/1998 | Ben-Haim | ............ 600/407 |
| 5,840,025 A | | 11/1998 | Ben-Haim | |
| 6,019,725 A | * | 2/2000 | Vesely et al. | ............ 600/447 |
| 6,226,542 B1 | * | 5/2001 | Reisfeld | ............ 600/407 |
| 6,556,695 B1 | | 4/2003 | Packer et al. | |
| 6,650,927 B1 | | 11/2003 | Keidar | |
| 2002/0065459 A1 | | 5/2002 | MacAdam et al. | |
| 2003/0018251 A1 | * | 1/2003 | Solomon | ............ 600/427 |
| 2004/0019447 A1 | * | 1/2004 | Shachar | ............ 702/115 |
| 2004/0078027 A1 | * | 4/2004 | Shachar | ............ 604/891.1 |
| 2004/0152974 A1 | | 8/2004 | Solomon | |
| 2005/0096589 A1 | * | 5/2005 | Shachar | ............ 604/95.01 |
| 2006/0114088 A1 | * | 6/2006 | Shachar | ............ 335/219 |
| 2006/0116634 A1 | * | 6/2006 | Shachar | ............ 604/95.01 |
| 2007/0055142 A1 | * | 3/2007 | Webler | ............ 600/425 |

FOREIGN PATENT DOCUMENTS

WO   WO 02/082375 A2   10/2002

* cited by examiner

*Primary Examiner*—Ruth S Smith
*Assistant Examiner*—Parikha S Mehta

(57) ABSTRACT

A method for providing measuring data for the precise local positioning of an ablation catheter comprises the recording of electrophysiological potential curves in a plurality of positions of the ablation catheter with regard to a potential measurement on a reference catheter. An x-ray image is recorded in each of the positions and the position of the ablation catheter in each instance on the x-ray image is characterized by a marker. The electrophysiological potential curves are coupled in a data-related manner with the markers. When a marker on the screen displaying the x-ray image is clicked on, the associated electrophysiological potential curves appear highlighted on another screen, if necessary in color or with increased brightness. Conversely, the x-ray image with the marker is queried, i.e. displayed and the marker highlighted when the potential curve is activated on a screen displaying the potential curve.

13 Claims, 1 Drawing Sheet

METHOD AND SYSTEM FOR CONCURRENT LOCALIZATION AND DISPLAY OF A SURGICAL CATHETER AND LOCAL ELECTROPHYSIOLOGICAL POTENTIAL CURVES

CROSS REFERENCE TO RELATED APPLICATIONS

This application claims priority to the German Application No. 10 2005 014 854.9, filed Mar. 30, 2005 which is incorporated by reference herein in its entirety.

FIELD OF INVENTION

The invention relates to a method for providing measuring data for the precise local positioning of an operation catheter, in particular an ablation catheter.

BACKGROUND OF INVENTION

An ablation catheter used with the operation concerning the heart serves to ablate tissue from the interior wall of the heart with the purpose of ablating (isolating) atrioventricular channels on the interior wall of the heart. The aim here is to remedy a medical condition relating to the functionality of the heart. This includes cardiac arrhythmias. One problem with different arrhythmias, for example with the AV Nodal Reentry Tachycardia, is that the abnormal area of the heart must be located, i.e. the best area for an ablation must be determined.

SUMMARY OF INVENTION

Two catheters are used for this, namely the operation catheter and the reference catheter. The reference catheter remains fixed. In specific chamber regions of the heart, the operation catheter is guided to different positions. In each position, signals of an electrophysiological potential curve are recorded by the operation catheter. This is set in each instance in relation to a potential measurement on the reference catheter. In particular, a temporal offset is determined between the reference catheter and the operation catheter. In other words, it is determined how to propagate signals in the heart. A signal can first be determined in the reference catheter and can then appear in the electrophysiological potential curve, which is recorded by the operation catheter. As corresponding signals repeatedly appear in the same manner, the same signal forms can be detected for the plurality of positions of the operation catheter. To determine the best area for an ablation, the site at which the earliest signal appears must be found, because the signal originates from the abnormal area. It regularly happens that said site of the earliest stimulation propagation has already been left, until it transpires that this is the site of the earliest stimulation propagation.

The problem for electrophysiologists who record the electrophysiological potential curves is therefore to deliver the catheter to an area where it has already previously been and for which the electrophysiological potentials have been recorded. On the basis of the potential curves, he has hitherto been able to orientate himself in the space, which however can lead to long examination times.

In order to support the electrophysiologist, a measuring method can also be used in a three-dimensional space. By way of example, the Carto positioning system by the company Biosense-Webster also uses an electromagnetic field, in which catheters equipped with coils are moved. The catheter position is indicated three-dimensionally in the virtual space on an additional workstation pertaining to the system. The complete system is very complex and expensive. The electrophysiologist must acquire an additional system. He can only use special and expensive catheters. In particular, catheters priced at approximately 2,500 euros each must be employed for single use.

It is an object of the invention to reliably but also cost-effectively assist the user (the electrophysiologist) with the precise local positioning of an operation catheter, in particular an ablation catheter.

The invention is based on the fact that nowadays, in every electrophysiological operation which executes ablations, an x-ray fluoroscopy system exists for the heart catheter, in addition to electrophysiological registration system. In accordance with the invention, an x-ray image is also recorded in each of the positions in which an electrophysiological potential curve is recorded. In the x-ray image, the operation catheter can be at least partially recognized. The position of the operation catheter can in each instance then be identified on the x-ray image by a marker.

The special feature of the invention is that the data from the electrophysiological potential curves is assigned to the markers, i.e. the data is 'interlinked'. This allows an associated electrophysiological potential curve to be queried when the marker is activated on a screen displaying the x-ray image, and/or conversely allows the x-ray image with the marker to be queried when the potential curve is activated on a screen displaying the potential curve.

The simplest method of activation is to click using a computer mouse (or a similar means such as a touchpad for instance), and the querying preferably results in a display on a screen. Potential curves and x-ray images are thus currently queried at the same time. Two screens thus exist, with the data being coupled to other data on the screen (interlinked). It would also be possible to display a part of the data in a screen segment, for instance, to show the electrophysiological potential curves in a segment on the x-ray screen.

With an alternative of the invention, the marker is set by an operator, preferably by clicking on a screen displaying the x-ray image.

Since the operation catheter has an easily recognizable form, e.g. a tip which can be recognized on an x-ray image, the marker can also be automatically set according to another alternative, with the aid of an image recognition system.

A plurality of different potential curves exists if the catheter passes through a plurality of positions. To facilitate the display of the data-related coupling, the different potential curves can be displayed in different colors, and the associated markers correspondingly displayed in the same color on the screen. Alternatively to the colors, specific forms of line comprising dashes or dashes and dots are possible, but colors can be recognized particularly quickly.

A color coding is preferably carried out as a function of a delay time of a signal from the potential curve compared with a reference signal in the reference catheter. As already mentioned above, this delay time allows the ideal site for the ablation to be determined. If a large delay time is now displayed for instance in dark blue and a very short delay time in red, a whole spectrum of colors from blue to red can be seen on the associated x-ray image, whereby when the color red is approached, the ideal site for the ablation is approached.

The data settings of the x-ray system, which serves to record the x-ray image, ideally remain the same throughout the whole time. The x-ray images can thus be superimposed on each other and the markers can be set in one individual image. The operation catheter is subsequently moved into the position meant for the ablation and an x-ray image is repeatedly recorded there. The electrophysiologist now examines whether this is the position which corresponds to the short delay time, e.g. an area marked with red, and thus knows whether the target point has been reached. If necessary, the operation catheter is moved a little again and a further x-ray image is recorded.

It can occasionally be necessary or advantageous to modify the data settings of the x-ray system while the ablation catheter is passing through the plurality of positions. Correspondingly, a number of x-ray images exist with the associated markers, with the corresponding x-ray image the being displayed after a respective potential curve has been activated (clicked-on) on the corresponding screen.

With a preferred embodiment, the data settings of the x-ray system are also indicated when the potential curve is activated. With a particularly preferred embodiment, the data settings on the x-ray system are recorded again when the potential curve is activated, for instance a repeated activation or activation using the right mouse button. By way of example, the C-arm of an x-ray angiography system can move into a specific position so as to repeat the recorded x-ray image. This enables the electrophysiologist to deliver the ablation catheter into the optimal position, after recording the different potential curves in the different positions, because the original recording situation, which has resulted in the x-ray image with the marker, is repeated.

The invention also relates to an x-ray recording system. This is connected to a registration system for recording electrophysiological potential curves via a data line, in particular a network link, such that it can exchange data with said registration system.

In an associated image processing system, the data from the x-ray recording system and the registration system can be coupled. In particular the x-ray recording system and the registration system are synchronized for instance via a network clock, so that the assignment of the data to one another is facilitated or even simply enabled.

The x-ray recording system is preferably an x-ray angiography system.

BRIEF DESCRIPTION OF THE DRAWINGS

A preferred embodiment of the invention is now described with reference to the drawing, in which.

DETAILED DESCRIPTION OF INVENTION

Figure 1:
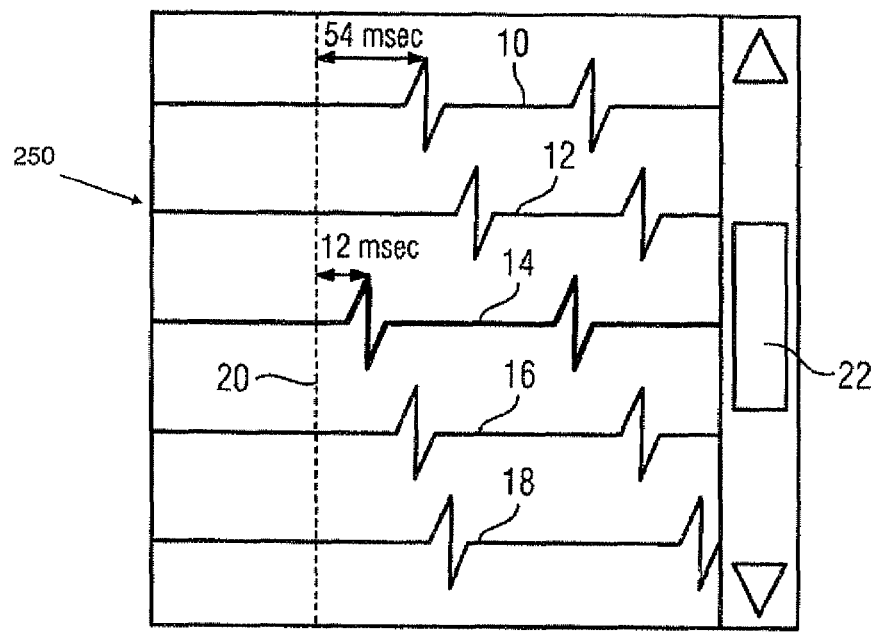
FIG. 1 shows a plurality of electrophysiological potential curves, and how they can be recorded in different positions of the ablation catheter.

FIG. 1 shows the screen 250 of an electrophysiological registration system 200 with five measuring curves 10, 12, 14, 16 and 18, which are recorded by an ablation catheter 210. Since an abnormal change in the heart appears in each heartbeat cycle, the curves 10, 12, 14, 16 and 18 have essentially the same form. The only differ in terms of their temporal insertion, the curves being in fact displayed in relation to a reference time, which is measured by the reference catheter and is indicated here by a dashed line 20. The dashed line corresponds with a reference pulse signal which the reference catheter receives and the ablation catheter receives this signal in a temporally displaced manner. By way of example, the delay time for the curve 10 and the curve 14 is shown. In the curve 10, the pulse which forms the main signal has a delay time of 54 msec compared with the reference catheter. For instance, the curve 10 was recorded here as the ablation catheter was located in an area which is displayed in FIG. 2 by the marked cross 110. Correspondingly, the potential curves 12, 14, 16 and 18 were recorded, as the ablation catheter was located in the area reproduced by the markers 112, 114, 116 and 118. Compared with the temporal zero point which is indicated by the curve 20, the potential curve 14 only features a delay of 12 msec. The delay time is not as minimal with any of the other curves. The site specified by the marker 114 is thus nearest to the site which is ideal for the ablation.

When recording the curves 10, 12, 14, 16 and 18, the electrophysiologist or an automatic system has set the markers 110, 112, 114, 116 and 118. The analysis of the electrophysiological potential curves 10 12, 14, 16 and 18 has now shown that the site 114 is best suited to an ablation. The potential curve 14 is thus marked in red (characterized here by a widening of the line) and the associated cross 114 is likewise marked in red. The other potential curves 10, 12, 16 and 18 can also be marked in color, as a function for instance of the time delay. The curve 10 could then be marked in yellow, the curve 18 in green and the curve 12 in blue. Accordingly, the crosses in FIG. 2 can also be color coded. A color nuancing towards yellow, green and blue thus results in both directions starting from the red point 114, downwards to the right and upwards to the left for instance.

Figure 2:
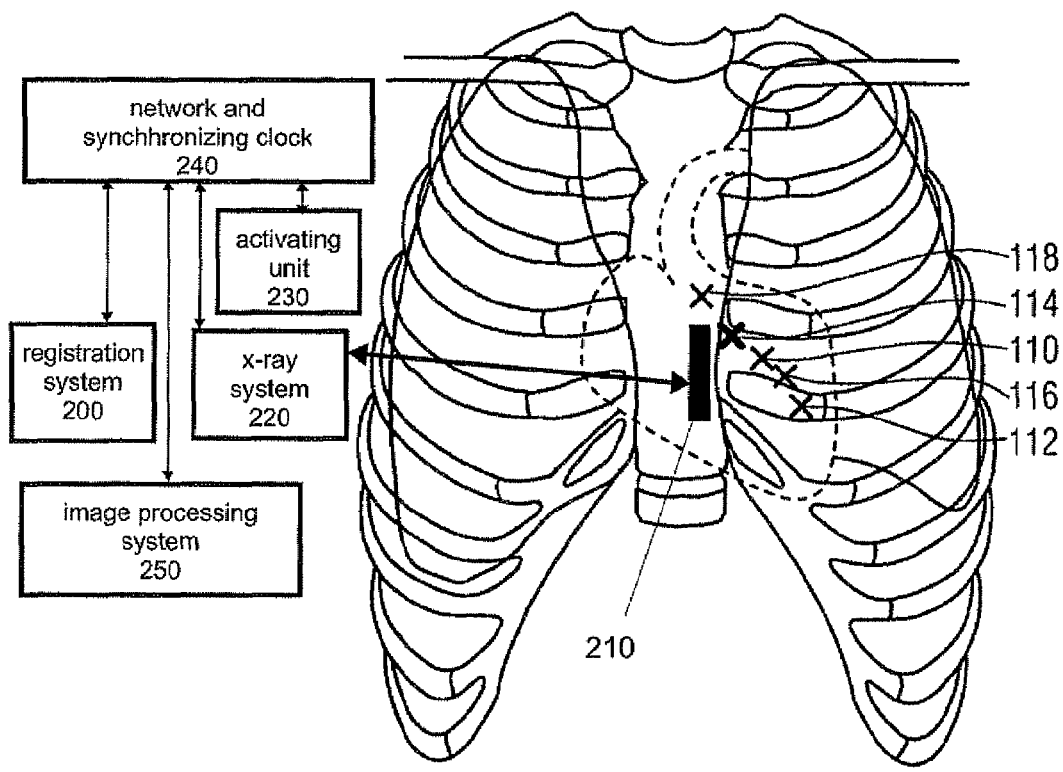
FIG. 2 shows a schematic representation of the body parts of a patient which can be recognized in an x-ray image, with markers having been set according to the invention in the x-ray image.

Further curves can be queried in the right of the screen 250 in FIG. 1 by the scroll-bar 22. The data from the screen shown in FIG. 1 is linked to the data from FIG. 2, i.e. the markers entered there, i.e. coupled in a data-related manner by the network and synchronizing clock 240. If one of the curves 10, 12, 14, 16 or 18 is clicked on by means of a mouse, not only does this curve light up more brightly, but so does the associated marker on the x-ray image from FIG. 2. If conversely the corresponding marker from the x-ray image from FIG. 2 is clicked-on by means of a mouse, the associated potential curve is correspondingly highlighted, e.g. in terms of color or brightness. The linking of the data allows electrophysiological potential curves to be precisely assigned to sites in the x-ray image at which the potential curves were recorded. If the electrophysiologist now wants to deliver the ablation catheter once more into the area predetermined by the marker 114, he should record another x-ray image from the position, as shown in FIG. 2. It is worth mentioning here that FIG. 2 with five markers is only possible if the same x-ray image is recorded five times from the same perspective, i.e. with the same basic settings of the x-ray system 220. To now move the ablation catheter to the area predetermined by the marker, he is best to reproduce the same recording situation. It is possible here, for instance, for the electrophysiologist to click the marker 114 on the x-ray image, which is shown in FIG. 2. If he repeats this clicking and activates the right mouse button/activating unit 230, the x-ray system moves back into the same position, in which he has recorded the x-ray image, which is shown schematically in FIG. 2. The electrophysiologist can then precisely deliver the ablation catheter to the exact site indicated by the marker 114.

A precise data-related assignment of the electrophysiological potential curves 10, 12, 14, 16 and 18 to corresponding markers 110, 112, 114, 116 and 118 on an x-ray image and a data-related coupling allows the data to be alternately queried between the two images displayed in FIG. 1 and FIG. 2, in other words alternately between the two different screens or screen parts. A click on an electrophysiological potential curve is sufficient to highlight the corresponding marker in the x-ray image. In contrast, a click on the marker is thus enough to show or highlight the corresponding electrophysiological potential curves on the other screen or screen element.

The invention claimed is:

1. A method of providing measuring data for a precise local positioning of a surgical catheter, comprising:
    recording electrophysiological potential curves at a plurality of positions of the surgical catheter in a vessel or organ by the surgical catheter;
    relating each recorded electrophysiological potential curve to an electric potential measurement executed by a reference catheter located in the vessel or organ;
    recording an x-ray image at each of the plurality of positions, each x-ray image at least partially showing the surgical catheter;
    marking a position of the surgical catheter in each x-ray image using markers;
    assigning the electrophysiological potential curves to the markers;
    displaying on a screen at least one of the x-ray images having at least one of the markers or displaying on the screen at least one of the recorded electrophysiological potential curves;
    activating the at least one marker of the displayed x-ray image or the at least one displayed electrophysiological potential curve; and
    querying and displaying such electrophysiological potential curve assigned to the activated marker or such x-ray image having such marker related to the activated electrophysiological potential curve,
    wherein different electrophysiological potential curves are displayed in different colors, and a related marker is displayed in such color corresponding to the respective electrophysiological potential curve, and
    wherein the different colors are determined by a color coding algorithm, the color coding algorithm based on a delay time of a signal included in the electrophysiological potential curves, the delay time of the signal calculated relative to a reference signal provided by the reference catheter.

2. The method according to claim 1, wherein the surgical catheter is an ablation catheter and wherein the electrophysiological potential curves are recorded using the ablation catheter.

3. The method according to claim 1, wherein the at least one marker is activated by clicking on the marker, and querying the related electrophysiological potential curve includes displaying the related electrophysiological potential curve on the screen.

4. The method according to claim 1, wherein marking the position of the surgical catheter in each x-ray image using the markers includes manually setting the markers on the screen by a user.

5. The method according to claim 1, wherein marking the position of the surgical catheter in each x-ray image using the markers includes automatically setting the markers by an image recognition system.

6. The method according to claim 1, further comprising assigning to each electrophysiological potential curve a current parameter setting of an x-ray system, the x-ray system used for recording the x-ray images and each current parameter setting corresponding to such recorded x-ray image related to the respective electrophysiological potential curve.

7. The method according to claim 6, further comprising displaying the current parameter setting upon activating the respective electrophysiological potential curve.

8. The method according to claim 7, further comprising re-adjusting the current parameter setting by the x-ray system upon activating the respective electrophysiological potential curve.

9. An x-ray recording system, comprising:
    a surgical catheter configured to acquire data for electrophysiological potential curves at a plurality of positions in a vessel or organ;
    an x-ray system configured to record an x-ray image at each position;
    a registration system connected to the x-ray system configured to record the electrophysiological potential curves;
    an activating unit configured to activate at least one of the recorded x-ray images or at least one of the recorded electrophysiological potential curves, and
    a screen, wherein the at least one activated recorded x-ray image or the at least one activated recorded electrophysiological potential curve is displayed on the screen,
    wherein the registration system is configured to interrelate the electrophysiological potential curves to the x-ray images such that upon activating the at least one recorded x-ray image's respective electrophysiological potential curve the interrelated electrophysiological potential curve respectively x-ray image is queried;
    wherein querying the interrelated electrophysiological potential curve respectively x-ray image includes displaying the interrelated electrophysiological potential curve respectively x-ray image on the screen,
    wherein different electrophysiological potential curves are displayed in different colors, and a related marker is displayed in such color corresponding to the respective electrophysiological potential curve, and
    wherein the different colors are determined by a color coding algorithm, the color coding algorithm based on a delay time of a signal included in the electrophysiological potential curves, the delay time of the signal calculated relative to a reference signal provided by the reference catheter.

10. The x-ray recording system according to claim 9, further comprising:
    an image processing system configured to combine data originating from the x-ray system and the registration system.

11. The x-ray recording system according to claim 9, further comprising:
    a synchronizing clock configured to synchronize the x-ray system and the registration system.

12. The x-ray recording system according to claim 11, wherein the x-ray system and the registration system are connected by a network, and the synchronizing clock is a network clock.

13. The x-ray recording system according to claim 9, wherein the x-ray recording system is an x-ray angiography system.

* * * * *